(12) United States Patent
Ravalico et al.

(10) Patent No.: US 9,308,560 B2
(45) Date of Patent: Apr. 12, 2016

(54) CLINICAL ANALYZER WASH AND METHOD

(71) Applicant: Abbott Laboratories, Abbott Park, IL (US)

(72) Inventors: Patricia H. Ravalico, Keller, TX (US); Charlie W. Wilson, III, Saginaw, TX (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 14/306,961

(22) Filed: Jun. 17, 2014

(65) Prior Publication Data

US 2014/0290706 A1 Oct. 2, 2014

Related U.S. Application Data

(60) Continuation of application No. 12/714,601, filed on Mar. 1, 2010, now Pat. No. 8,759,106, which is a division of application No. 10/158,495, filed on May 29, 2002, now abandoned.

(51) Int. Cl.
*B08B 3/04* (2006.01)
*G01N 35/10* (2006.01)
*B08B 3/02* (2006.01)

(52) U.S. Cl.
CPC .............. *B08B 3/04* (2013.01); *G01N 35/1004* (2013.01); *B08B 3/02* (2013.01); *G01N 35/10* (2013.01); *G01N 2035/1006* (2013.01); *Y10T 436/114998* (2015.01); *Y10T 436/115831* (2015.01); *Y10T 436/12* (2015.01)

(58) Field of Classification Search
CPC ................................................. G01N 35/1004
See application file for complete search history.

(56) References Cited

U.S. PATENT DOCUMENTS

| 4,276,051 | A | 6/1981 | Ginsberg et al. |
|---|---|---|---|
| 5,186,194 | A | 2/1993 | Kitajima |
| 5,320,809 | A | 6/1994 | Dunn et al. |
| 5,408,891 | A | 4/1995 | Barber et al. |
| 5,592,959 | A | 1/1997 | Nagai |
| 5,827,744 | A | 10/1998 | Fose et al. |

(Continued)

FOREIGN PATENT DOCUMENTS

| CA | 2103384 | 7/2005 |
|---|---|---|
| EP | 0251087 | 1/1988 |

(Continued)

OTHER PUBLICATIONS

Canadian Office Action, issued by the Canadian Intellectual Property Office, in connection with corresponding Canadian patent application No. 2,486,264, on Apr. 20, 2010, 3 pages.

(Continued)

*Primary Examiner* — Jill Warden
*Assistant Examiner* — Matthew Krcha
(74) *Attorney, Agent, or Firm* — Hanley, Flight & Zimmerman, LLC

(57) ABSTRACT

A clinical analyzer has been described that includes a probe to aspirate a fluid. The probe is washed between aspirations to reduce carryover. The wash operation includes both an internal and an external wash, where the internal wash operation is terminated prior to terminating the external wash. In one example, the probe wash can be implemented on an integrated clinical chemistry/immunoassay analyzer.

12 Claims, 5 Drawing Sheets

(56) References Cited

U.S. PATENT DOCUMENTS

| | | | |
|---|---|---|---|
| 6,027,691 | A | 2/2000 | Watts et al. |
| 6,422,248 | B1 | 7/2002 | Furst et al. |
| 6,498,037 | B1 | 12/2002 | Carey et al. |
| 2002/0012916 | A1 | 1/2002 | Gundling et al. |
| 2002/0185161 | A1 | 12/2002 | Furst et al. |

FOREIGN PATENT DOCUMENTS

| | | |
|---|---|---|
| EP | 0602802 | 6/1994 |
| EP | 0661542 | 7/1995 |
| EP | 1087231 | 3/2001 |
| JP | 06213906 | 8/1994 |
| JP | 06222065 | 8/1994 |
| JP | 07174765 | 7/1995 |
| JP | 07229905 | 8/1995 |
| JP | 2000046844 | 2/2000 |
| WO | 9735173 | 9/1997 |

OTHER PUBLICATIONS

Canadian Office Action, issued by the Canadian Intellectual Property Office, in connection with corresponding Canadian patent application No. 2,486,264, on Jul. 13, 2011, 2 pages.
Canadian Office Action, issued by the Canadian Intellectual Property Office, in connection with corresponding Canadian patent application No. 2,486,264, on Nov. 5, 2012, 2 pages.
European Office Action, issued by the European Patent Office in connection with European Patent Application 03 756 244.4, on Dec. 7, 2010, 8 pages.
International Search Report, issued by the International Searching Authority in connection with corresponding International patent application No. PCT/US2003/016872 mailed on Jan. 21, 2004, 5 pages.
Notice of Rejection, English Language, issued by the Intellectual Property Office of Japan, in connection with Japanese application No. 2010-046040 on Dec. 20, 2011, 4 pages.
Notice of Rejection, English Language, issued by the Intellectual Property Office of Japan, in connection with Japanese application No. 2010-046040 on Oct. 9, 2012, 4 pages.
Examiner's Decision of Rejection, English Language, issued by the Intellectual Property Office of Japan, in connection with Japanese application No. 2010-046040 on Apr. 23, 2013, 4 pages.
Restriction and/or Election Requirement, issued by the United States Patent and Trademark Office in connection with U.S. Appl. No. 10/158,495 on Oct. 6, 2005, 5 pages.
Office Action, issued by the United States Patent and Trademark Office in connection with U.S. Appl. No. 10/158,495, on Aug. 1, 2006, 9 pages.
Final Rejection, issued by the United States Patent and Trademark Office in connection with U.S. Appl. No. 10/158,495, on Apr. 30, 2007, 7 pages.
Final Rejection, issued by the United States Patent and Trademark Office in connection with U.S. Appl. No. 10/158,495, on Sep. 10, 2007, 9 pages.
Decision on Appeal, issued by the United States Patent and Trademark Office Board of Patent Appeals and Interferences in connection with U.S. Appl. No. 10/158,495, on Feb. 18, 2010, 13 pages.
Office Action, issued by the United States Patent and Trademark Office in connection with U.S. Appl. No. 12/714,601, on Jun. 24, 2010, 10 pages.
Restriction and/or Election Requirement, issued by the United States Patent and Trademark Office in connection with U.S. Appl. No. 12/714,601 on Feb. 17, 2011, 5 pages.
Final Rejection, issued by the United States Patent and Trademark Office in connection with U.S. Appl. No. 12/714,601, on May 19, 2011, 10 pages.
Miscellaneous Office Action, issued by the United States Patent and Trademark Office in connection with U.S. Appl. No. 12/714,601, on Apr. 12, 2013, 5 pages.
Office Action, issued by the United States Patent and Trademark Office in connection with U.S. Appl. No. 12/714,601, on Jul. 23, 2013, 9 pages.
Final Rejection, issued by the United States Patent and Trademark Office in connection with U.S. Appl. No. 12/714,601, on Nov. 5, 2013, 9 pages.
Notice of Allowance and Fee(s) Due, issued by the United States Patent and Trademark Office in connection with U.S. Appl. No. 12/714,601, on Feb. 12, 2014, 15 pages.
Examiner's Answer, issued by the United States Patent and Trademark Office in connection with U.S. Appl. No. 10/158,495, on Jun. 27, 2008, 10 pages.

CLINICAL ANALYZER WASH AND METHOD

RELATED APPLICATIONS

This patent is a continuation of U.S. patent application Ser. No. 12/714,601, filed Mar. 1, 2010, entitled "Clinical Tester Wash and Method," which is a divisional application of and claims priority to U.S. patent application Ser. No. 10/158,495, filed May 29, 2002, entitled "Clinical Analyzer Wash and Method." U.S. patent application Ser. Nos. 12/714,601 and 10/158,495 are hereby incorporated by reference in their entireties.

FIELD OF THE DISCLOSURE

The present disclosure relates generally to clinical test equipment and in particular the present disclosure relates to reduction of sample carryover in clinical test equipment.

BACKGROUND

Although various known clinical analyzers for chemical, immunochemical and biological testing of samples are available, clinical technology is rapidly changing due to increasing demands in the clinical laboratory to provide new levels of service. These new levels of service must be more cost effective to decrease the operating expenditures such as labor cost and the like, and must provide shorter turnaround time of test results. Modernization of analytical apparatus and procedure demands consolidation of workstations to meet the growing challenge placed on clinical laboratories.

Generally, analysis of a test sample involves the reaction of test samples with one or more reagents with respect to one or more analytes wherein it is frequently desired that the analysis be performed on a selective basis with respect to each test sample. Automated clinical analysis systems analyze a test sample for one or more characteristics. Automated clinical analyzers also provide results much more rapidly while frequently avoiding operator or technician error, thus placing emphasis on accuracy and repeatability of a variety of tests. Automated clinical analyzers presently available for routine laboratory tests include a transport or conveyor system designed to transport containers of sample liquids between various operating stations.

Some of the presently available automated clinical analyzers, such as automated immunoassay analyzers, utilize procedures involving a variety of different assay steps. A robotic arm automatically processes the test samples with a probe and a carousel, or robotic track, which positions the samples for processing. A typical analyzer has a sample probe to sample fluids and deposit the samples in a reaction vessel. One or more reagents are added to the vessel using reagent probes. Sample and reagent probe arms include probes that can be moved between sample or reagent locations, the reagent vessel and wash stations.

Clinical chemistry and immunoassay analyzers have traditionally been standalone systems. These systems can be combined using a common transport system to provide a more efficient integrated system. Previous standalone chemistry analyzers did not require sample-to-sample carryover performance requirements of an integrated clinical chemistry and immunoassay system. As laboratories integrate automated analytical systems, reduction of between-sample carryover becomes a critical goal. Many companies have elected to overcome this problem through use of disposable probe tips, but this approach is costly, wasteful and less reliable. Another safeguard is to prioritize test sequencing such that immunoassay sampling is done prior to all chemistry tests. This approach impacts chemistry turnaround time and lowers total workflow throughput. Yet another method to reduce sample carryover is to flush the system with large amounts of fluids (buffer, water, detergents).

For the reasons stated above, and for other reasons stated below which will become apparent to those skilled in the art upon reading and understanding the present specification, there is a need in the art for a reduction in sample carryover in clinical test equipment.

SUMMARY

The above-mentioned problems with sample carryover and other problems are addressed by the present disclosure and will be understood by reading and studying the following specification.

In one example, a clinical analyzer comprises a probe having an interior region and an exterior surface. The probe is used to selectively aspirate a fluid into the interior region. A first wash mechanism is coupled to the probe to dispense a wash fluid through the interior region of the probe for a first predetermined period. A second wash mechanism is located to dispense the wash fluid on the exterior surface of the probe for a second predetermined period. The second predetermined period extends beyond the first predetermined period.

In another example, a method of cleaning a probe comprises flushing an interior region of the probe with a wash fluid for X seconds, and simultaneously flushing an exterior surface of the probe with the wash fluid for Y seconds, wherein Y is greater than X.

A method for reducing sample carryover in an integrated chemistry and immunoassay analyzer comprises aspirating a first test sample from a first sample container using a probe, depositing the first test sample into a reaction vessel and performing a chemical analysis of the test sample. The probe is washed by pumping a wash fluid through an interior region of the probe and pumping the wash fluid on the exterior of the probe. The pumping of the wash fluid into the interior region is terminated prior to terminating the pumping of the wash fluid to the exterior. A second test sample is then aspirated from a second sample container using the probe.

DETAILED DESCRIPTION

Figure 1A:
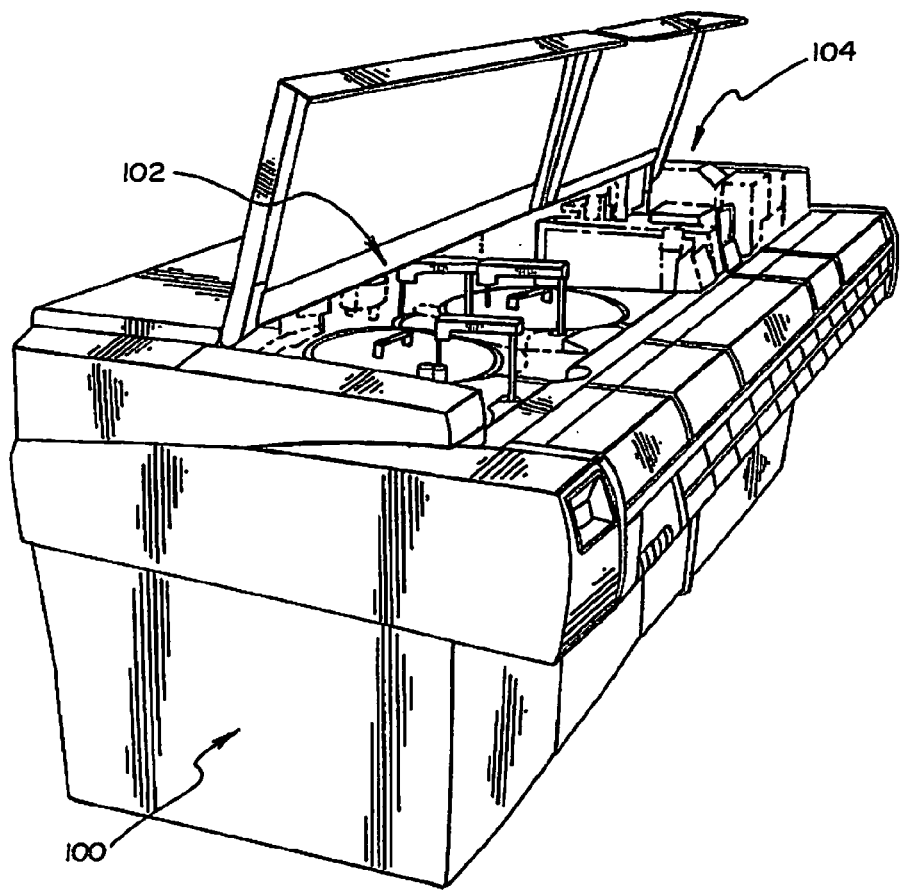
FIG. 1A is a perspective view of an example clinical analyzer.

In the following detailed description of the preferred examples, reference is made to the accompanying drawings, which form a part hereof, and in which is shown by way of illustration specific preferred examples in which the disclosure may be practiced. These examples are described in sufficient detail to enable those skilled in the art to practice the disclosure, and it is to be understood that other examples may be utilized and that logical, mechanical and electrical changes may be made without departing from the spirit and scope of the present disclosure. The following detailed description is, therefore, not to be taken in a limiting sense, and the scope of the present disclosure is defined only by the claims.

The term "test sample", as used herein, refers to a test material that can be used directly as obtained from a source or following a pretreatment to modify the character of the sample. The test sample can be derived from any biological source, such as physiological fluid, including, whole blood, serum, plasma, saliva, ocular lens fluid, cerebral spinal fluid, sweat, urine, milk, ascites fluid, raucous, synovial fluid, peritoneal fluid, amniotic fluid or the like.

The term "carryover" refers to cross-contamination or contact transfer between test samples. Carryover is a byproduct of using a common sample probe for multiple test samples.

Between-sample carryover is a critical factor to ensure result integrity on automated analytical systems Immunoassay analyzers traditionally meet a sample-to-sample carryover goal of less than 0.1 ppm. Clinical chemistry systems utilize methodologies that are less sensitive and rarely characterized using carryover requirements to this level. As laboratories consolidate analytical systems, however, the between-sample carryover demands for immunoassay analyzers become applicable to clinical chemistry systems as well. Achieving a between-sample carryover goal of less than 0.1 ppm for an integrated immunoassay and clinical chemistry system can impact marketability of other variables including specimen throughput, system consumables, test prioritization, and sample pre-aliquoting.

Extensive research on an integrated system of an example of the present disclosure identified critical variables associated with sample-to-sample carryover. High-speed video was used for qualitative characterization of the sample probe wash while concentrated samples of hepatitis surface-antigen (HbsAg) were used to quantitatively assess carryover performance. A probe wash protocol of an example of the disclosure passes the between-sample carryover limit of 0.1 ppm without sample pre-aliquoting, use of additional consumables, test prioritization, or significant impact to system specimen throughput. Critical variables include clinical chemistry sampling/aspiration volumes and external sample probe wash duration, sequencing relative to the internal sample probe wash. Other variables include positioning of the sample probe within the sample wash cup, sample wash cup design and external sample wash flow volumes/rates.

An example of a wash protocol dictates the between sample wash mechanism based on clinical chemistry sampling volume. The wash includes an external wash and an internal wash of the sample probe. All specimens with a maximum chemistry sampling volume below a predetermined threshold (such as 15 µL or less) are effectively washed using an extended single cycle wash mechanism. It is noted that a 'dummy' fluid volume may be aspirated in addition to the fluid sample volume. The dummy volume provides a buffer between the sample fluid and residual fluid in the probe. The dummy volume is not included in the sample volume levels described herein. The extended single cycle wash mechanism utilizes a one second external probe wash that ends 100 ms after the internal probe wash. This timing relationship between the internal and external wash sequencing is particularly crucial for acceptable carryover performance. Specimens that are processed with chemistry sampling volumes exceeding the threshold (15.1 µL or more) are washed using the same extended single cycle wash mechanism but also undergo an additional 3.2 seconds of supplemental external wash. The wash protocol of the present disclosure, as explained below, is not limited to a specific timing duration or over-lap time between the termination of internal and external washes.

Between-Sample Carryover was quantitatively evaluated using recombinant samples of concentrated hepatitis surface-antigen (HbsAg) in a pooled human serum matrix. Each concentrated HBsAg sample (with approximate immuno-reactivity of 4 mg/mL) was followed by pooled normal human serum (pre-screened non-reactive for HbsAg) and processed on a chemistry analyzer. The pooled human serum samples were evaluated on an immunoassay analyzer for HbsAg activity. Results were compared against serial dilutions of the concentrated stock. If the pooled human serum results exceeded that of the 0.1 ppm dilution of the concentrated stock, a test run was considered a failure. The magnitude of the failure was calculated by converting the reported concentration of the serum diluents into units of ppm from the reference dilution. Test conditions were created to represent worst-case performance and test result confidence. The clinical chemistry sample volume was defined at 35 µL, a typical maximum sample volume for a chemistry application. HbsAg samples were processed in duplicate to ensure result integrity.

Results demonstrated a sample carryover performance trend associated with sample probe aspiration volume. As the clinical chemistry sample volume increases, between-sample carryover failures also increase. Most systems fail between-sample carryover with a frequency higher than 50% (without optimization critical parameters) at the maximum clinical chemistry sampling volume of 35 µL. The relationship between sample volume and sample-to-sample carryover performance is significant to understanding the mode of failure. This is because trending demonstrates that internal contamination of the sample probe has an impact on sample-to-sample carryover. The sample probe aspirates a test sample from a sample tube and immediately dispenses the sample volume into a reaction vessel prior to entrance into a wash station. An over-aspiration or dummy volume is dispensed at the wash station but this volume is consistent and independent of chemistry sample volume (under the protocol test conditions). Since the frequency of the carryover increases with chemistry sample volume and since this sample volume is dispensed prior to external wash of the probe, it was theorized that the source of the carryover (leading to the between-sample failures) resulted from internal contamination of the sample probe. This theory was supported by a supplemental investigation that demonstrated that carryover failures were still prevalent without any dummy/over aspiration being dispensed at the sample wash station. Residual carryover remained on the external surface of the sample probe following sample probe washing, even when the probe did not dispense any concentrated sample at the wash station. The frequency of sample carryover failures can be reduced using supplemental probe washes. Unfortunately, supplemental washes require additional instrument cycles that can degrade system specimen throughput.

A second variable to carryover performance is wash sequencing at the sample wash station. Further analysis of wash conditions at the sample wash station lead to a study evaluating external wash sequencing relative to the internal wash. Success of the probe wash was less dependent on the external wash duration than it was on the stop sequencing of the external wash relative to the internal wash. If the internal wash stops after the external wash, carryover performance is significantly worse than if the external wash ends after the internal wash. This relationship supports a theory that internal contamination of the probe is a source for the external between-sample carryover. One wash protocol utilizes a one second external probe wash that extends beyond the stop time of the internal wash to improve carryover performance at low sample volumes. A supplemental washing that would have required an additional instrument cycle is not required to meet carryover performance criteria.

Further studies demonstrated additional variables associated with between-sample carryover performance. These include wash cup design, hardware alignment at the sample wash station, and wash flow rates/volume. These variables are significant and require optimization for carryover performance. Failure to optimize these parameters can cause carryover failures. However, optimization, of these parameters will not create a passing condition without control of the critical variables of chemistry sampling volume and wash sequencing.

Figure 1B:
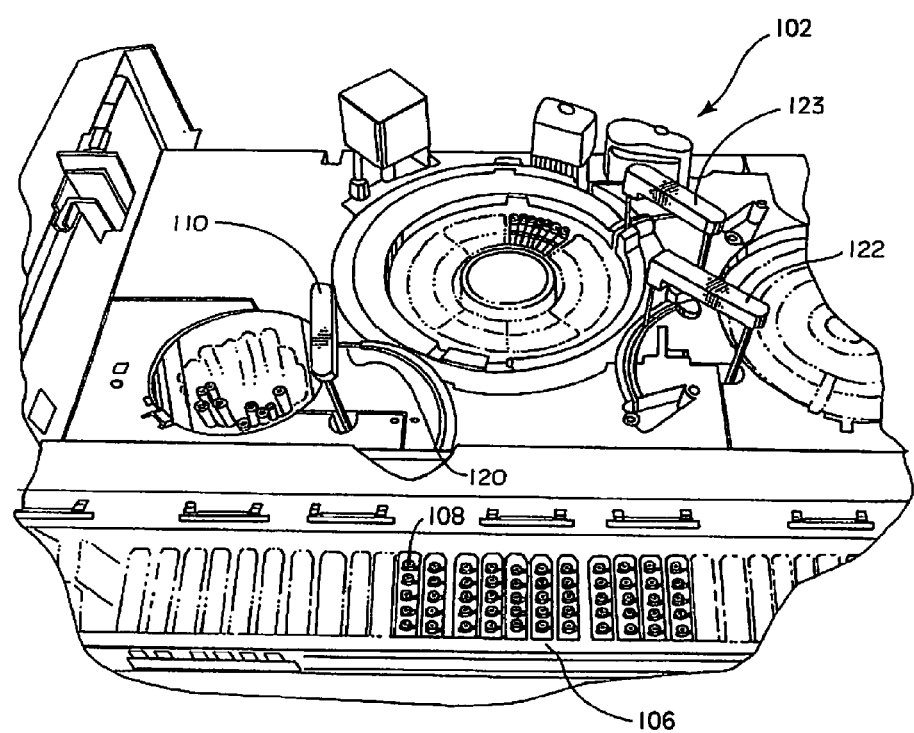
FIG. 1B is a clinical chemistry analyzer of the analyzer of FIG. 1A.

Referring to FIG. 1A, a perspective view of a simplified integrated clinical test system 100 of an example of the present disclosure. The test system includes a clinical chemistry analyzer 102 and an immunoassay analyzer 104, see FIGS. 1B and 1C for more detail. The two analyzers share a common sample transporter 106 that allows linear movement of test sample tubes 108 between the two analyzers.

Figure 2:
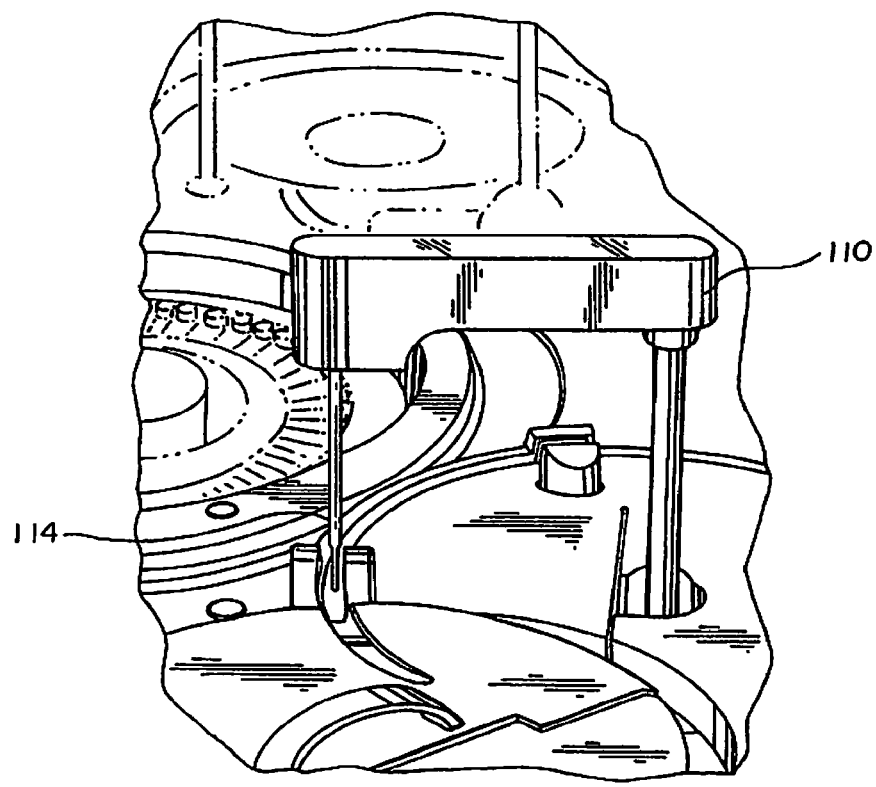
FIG. 2 illustrates a probe arm of the clinical analyzer of FIG. 1.

Each analyzer has a sample probe arm 110/112 that includes a sample probe 114 (see FIG. 2). The sample probe arms 110/112 can move in both a horizontal arc and vertical directions. The sample probe 114 aspirates a test sample from tube 108 located on the transporter 106. The sample probe 114 is then moved to a sample vessel (not shown) and deposits the aspirated sample. After the sample has been discharged from the sample probe 114, the sample probe arm 110/112 moves to a wash station 120 where the sample probe 114 is washed. The sample vessel is moved to a location where a reagent is added to the sample by a reagent probe of a reagent probe arm 122. The reagent probe arm 122 is movable between a reagent location, the sample vessel and the wash station. The sample vessel may receive additional reagents and is then subjected to chemistry testing, as known to those skilled in the art. A second reagent probe of a second reagent probe arm 123 can be included to provide a second reagent to the sample vessel.

Figure 1C:
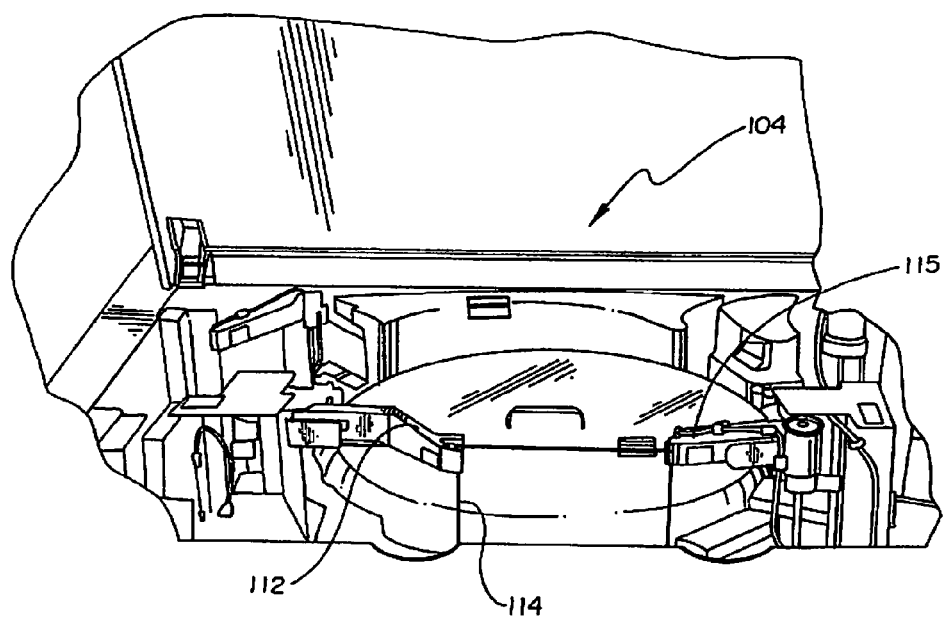
FIG. 1C is an immunoassay analyzer of the analyzer of FIG. 1A.

The sample tube 108 located on the transporter 106 is then moved to a location near the immunoassay analyzer 104, FIG. 1C. The immunoassay analyzer is similar in operation to the clinical chemistry analyzer in that a test sample from the sample tube is aspirated using sample probe 114 of sample probe arm 110/112. The sample probe arm 110/112 then moves to a sample vessel (not shown) and the sample probe 114 deposits the aspirated sample. After the sample has been discharged from the sample probe 114, the sample probe arm 110/112 moves to a wash station (not shown) where the sample probe 114 is washed. The sample vessel is moved to a location where a reagent is added to the sample by a reagent probe of a reagent probe arm 115. The reagent probe arm 115 is movable between a reagent location, the sample vessel and the wash station. The sample vessel may receive additional reagents and is then subjected to testing, as known to those skilled in the art. It is clear that sample carryover, or contamination, can occur if the sample probes 114 are not cleaned between aspirations of different test samples.

FIG. 2 illustrates a sample probe arm 110. The sample probe arm 110 includes a sample probe 114 that can be moved about a horizontal arc and in a vertical direction. The sample probe 114 has a hollow bore that allows aspiration of a fluid and the subsequent introduction of a wash fluid. The mechanics of the sample probe arm 110 are not described in detail herein, but are generally known to those skilled in the art. For purposes of understanding the disclosure, the sample probe arm 110 is controllable to regulate the amount of sample aspirated and the amount and duration of wash fluid that flows through the sample probe 114.

Figure 3:
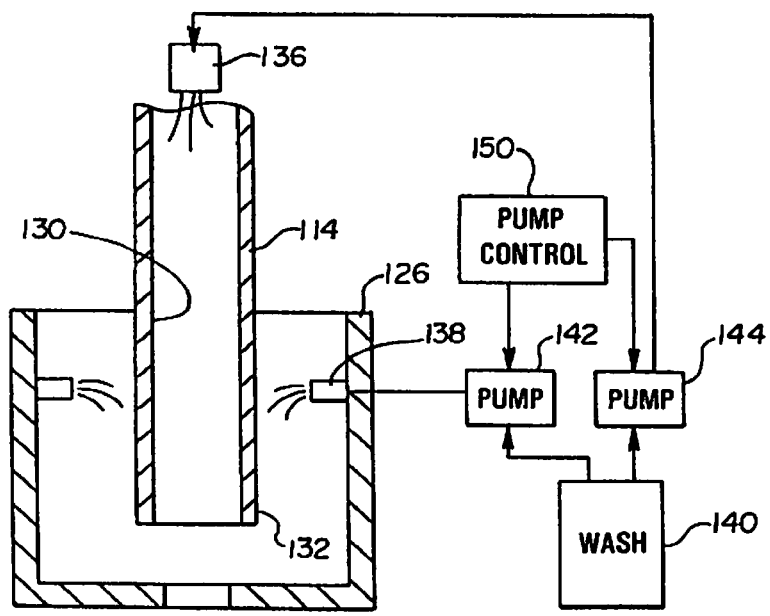
FIG. 3 is a simplified cross-section of a probe in a wash station.

Referring to FIG. 3, a cross-sectional view of a sample probe 114 and wash cup 126 are illustrated. The size and shape of the sample probe 114 and wash cup 126 are illustrative only and not intended to reflect actual designs or sizes. Those skilled in the art with the benefit of the present description will appreciate that the designs of the sample probe 114 and wash cup 126 can vary without departing from the present disclosure. The sample probe 114 is substantially tube-shaped and includes an exterior surface 132 and an interior surface 130. An interior wash dispenser 136, or nozzle, is located to discharge a wash fluid into the interior region of the sample probe 114. During a wash operation, the sample probe 114 is vertically positioned in the wash cup 126. The wash cup 126 includes one or more exterior wash dispensers 138, or nozzles, positioned to spray a wash fluid toward a center region of the wash cup 126 and onto the exterior surface 132 of the sample probe 114.

The wash fluid pumped through the interior region of the sample probe 114 and on its exterior surface 132 is the same fluid and depends upon the material that is to be removed from the sample probe 114. The wash fluid can be located in a common reservoir 140 and pumped to the nozzles using separate pumps 142 and 144. Alternately, a single pump and controllable valves can be used to pump the wash fluid to the nozzles. The present disclosure is not limited to a specific pump design, provided the termination of the flow of the internal fluid and the external fluid can be separately controlled by pump(s) controller 150. The term 'pump' is intended to include any mechanism that allows for controlled movement of a liquid, such as the wash fluid.

As explained above, a given probe needs to be sufficiently cleaned between aspirations to reduce liquid carryover. The liquid carryover can be that of a test sample or a reagent depending upon the probe. The internal wash is terminated prior to terminating the external wash. This termination overlap significantly reduces liquid carryover and allows clinical chemistry analyzers to meet the restrictive specifications of immunoassay analyzers. One example wash for chemistry sampling volume below a predetermined threshold (such as 15 µL or less) includes a one second external sample probe wash that ends 100 ms after the internal sample probe wash ends. The external wash can begin prior to the internal wash without departing from the present disclosure.

The present disclosure is not limited to an integrated clinical chemistry/immunoassay analyzer, and other analytical systems can utilize the relationship of between-sample carryover performance to improve sample wash parameters. This includes other clinical chemistry and immunoassay systems as well as hematology and other methodologies. The wash method can also be used utilized for reagent carryover washing, sample pretreatment instrumentation, and with laboratory automation systems.

CONCLUSION

A clinical analyzer has been described that includes a probe to aspirate a fluid. The probe is washed between aspirations to reduce carryover. The wash operation includes both an internal and an external wash, where the internal wash operation is terminated prior to terminating the external wash. In one example, the probe wash can be implemented on an integrated clinical chemistry/immunoassay analyzer.

Although specific examples have been illustrated and described herein, it will be appreciated by those of ordinary skill in the art that any arrangement, which is calculated to achieve the same purpose, may be substituted for the specific example shown. This application is intended to cover any adaptations or variations of the present disclosure. Therefore, it is manifestly intended that this disclosure be limited only by the claims and the equivalents thereof.

What is claimed is:

1. A system comprising:
   an interior wash dispenser;
   an exterior wash dispenser;
   a first pump to pump wash fluid through the exterior wash dispenser onto an exterior surface of a probe;
   a second pump to pump wash fluid through the interior wash dispenser into an interior region of the probe and
   a controller to:
      activate the first pump to pump wash fluid on the exterior surface of the probe;
      activate the second pump to pump wash fluid through the interior region of the probe simultaneously as the first pump is pumping wash fluid on the exterior surface of the probe, the second pump activated after the first pump is activated;
      deactivate the second pump to terminate pumping wash fluid through the interior region of the probe; and
      deactivate the first pump to terminate pumping wash fluid on the exterior surface of the probe after the second pump is deactivated, wherein a duration of time of activation of the first pump to wash the exterior surface of the probe is based on an amount of liquid aspirated into the interior region of the probe.

2. The system of claim 1, wherein the controller is configured to activate the first pump to pump wash fluid on the exterior surface of the probe for a first duration of time if the amount of liquid aspirated inside the probe is less than a threshold, and the controller is configured to activate the first pump to pump wash fluid onto the exterior surface of the probe for a second duration of time if the amount of liquid aspirated inside the probe is greater than the threshold, the second duration of time being greater than the first duration of time.

3. The system of claim 2, wherein the first duration of time is about one second.

4. The system of claim 3, wherein the second duration of time is about 4.2 seconds.

5. The system of claim 2, wherein the threshold is about 15 micro-liters.

6. The system of claim 1, wherein the controller is configured to deactivate the first pump after a period of time after deactivation of the second pump, the period of time about equal to about one-tenth an amount of the time the first pump was activated.

7. The system of claim 1, wherein the controller is configured to deactivate the first pump about 0.1 second after the second pump is to be deactivated.

8. The system of claim 1 further comprising a reservoir to contain the wash fluid, wherein the first pump and the second pump draw the wash fluid from the reservoir.

9. The system of claim 1, wherein the liquid is a test sample or a reagent used by a clinical chemistry analyzer or an immunoassay analyzer.

10. The system of claim 1, wherein the wash fluid to be pumped through the interior region of the probe is the same type as the wash fluid to be pumped on the exterior surface of the probe.

11. The system of claim 10, wherein the type of wash fluid used is based on the type of liquid aspirated by the probe.

12. The system of claim 1, further including a wash cup which contains the exterior wash dispenser.

* * * * *